United States Patent
Magni et al.

(10) Patent No.: US 7,228,067 B2
(45) Date of Patent: Jun. 5, 2007

(54) CHROMATOGRAPHY COLUMN ASSEMBLY WITH WOVEN TUBULAR MESH HEATER ELEMENT

(75) Inventors: Paolo Magni, Milan (IT); Giacinto Zilioli, Milan (IT); Riccardo Facchetti, Lecco (IT)

(73) Assignee: Thermo Finnigan Italia S.p.A., Rodano, Milan (IT)

( * ) Notice: Subject to any disclaimer, the term of this patent is extended or adjusted under 35 U.S.C. 154(b) by 301 days.

(21) Appl. No.: 10/181,143

(22) PCT Filed: Oct. 29, 2001

(86) PCT No.: PCT/IB01/02037

§ 371 (c)(1),
(2), (4) Date: Oct. 8, 2002

(87) PCT Pub. No.: WO02/40988

PCT Pub. Date: May 23, 2002

(65) Prior Publication Data

US 2003/0053800 A1    Mar. 20, 2003

(30) Foreign Application Priority Data

Nov. 15, 2000    (IT) .......................... MI2000A2449

(51) Int. Cl.
*F24H 1/10* (2006.01)
(52) U.S. Cl. ..................... 392/480; 219/528
(58) Field of Classification Search ................ 342/480, 342/481, 482, 472; 219/528, 529, 535, 545, 219/549; 338/208; 73/863.11, 23.39, 23.35, 73/61.52, 61.53, 23.25; 96/101; 422/89
See application file for complete search history.

(56) References Cited

U.S. PATENT DOCUMENTS

| | | | | |
|---|---|---|---|---|
| 787,047 A | * | 4/1905 | Leonard | 338/266 |
| 1,905,343 A | * | 4/1933 | Carpenter | 392/472 |
| 2,758,194 A | * | 8/1956 | Heron | 392/472 |
| 3,063,286 A | * | 11/1962 | Nerheim | 73/23.41 |
| 3,336,792 A | * | 8/1967 | Boys | 73/23.38 |
| 3,522,413 A | | 8/1970 | Chrow | |
| 3,791,415 A | * | 2/1974 | Lawless et al. | 138/127 |
| 4,352,007 A | * | 9/1982 | Baker et al. | 392/472 |
| 4,484,061 A | * | 11/1984 | Zelinka et al. | 392/468 |
| 4,726,822 A | * | 2/1988 | Cates et al. | 96/101 |
| 5,005,399 A | | 4/1991 | Holtzclaw et al. | |

(Continued)

FOREIGN PATENT DOCUMENTS

DE    3332551    * 3/1985

(Continued)

OTHER PUBLICATIONS

Ehrmann et al., "Novel Column Heater For Fast Capillary Gas Chromatography", *Journal of Chromatographic Science*, vol. 34, Dec. 1996, pp. 533-539.

*Primary Examiner*—Thor S. Campbell
(74) *Attorney, Agent, or Firm*—Nixon & Vanderhye P.C.

(57) ABSTRACT

A direct-heating column assembly for chromatography, includes at least one capillary column and at least one element made of electrically conductive material in contact with the capillary column. The element includes a plurality of filaments woven together to form a tubular mesh that uniformly envelops the outer surface of the capillary column both in radial and longitudinal directions.

25 Claims, 2 Drawing Sheets

U.S. PATENT DOCUMENTS

| | | | |
|---|---|---|---|
| 5,114,439 A | 5/1992 | Yost et al. | |
| 5,394,507 A * | 2/1995 | Okamoto | 392/480 |
| 5,544,276 A | 8/1996 | Loux et al. | |
| 5,600,752 A * | 2/1997 | Lopatinsky | 392/488 |
| 5,611,846 A | 3/1997 | Overton et al. | |
| 5,744,206 A | 4/1998 | Russek et al. | |
| 5,808,178 A | 9/1998 | Rounbehler et al. | |
| 6,049,658 A * | 4/2000 | Schave et al. | 392/472 |
| 6,209,386 B1 * | 4/2001 | Mustacich et al. | 73/23.39 |
| 6,217,829 B1 * | 4/2001 | Mustacich et al. | 422/89 |
| 2005/0084255 A1 * | 4/2005 | Kertesz | 392/480 |

FOREIGN PATENT DOCUMENTS

| | | | |
|---|---|---|---|
| DE | 29613330 | * | 9/1996 |
| FR | 2603086 | * | 2/1988 |
| IT | MI99A002708 | | 12/1999 |
| JP | 10-26286 | * | 1/1988 |
| JP | 63-48450 | * | 3/1988 |
| JP | 4-206382 | * | 7/1992 |
| JP | 11-62556 | * | 3/1999 |
| JP | 11-149978 | * | 6/1999 |
| NL | 9100364 | * | 9/1992 |
| WO | 99/33326 | * | 7/1999 |

\* cited by examiner

CHROMATOGRAPHY COLUMN ASSEMBLY WITH WOVEN TUBULAR MESH HEATER ELEMENT

CROSS-REFERENCE TO RELATED APPLICATION

This is a national phase application of International Application No. PCT/IB01/02037, filed Oct. 29, 2001, which claims the benefit of Italian Application No. MI2000A002449, filed Nov. 15, 2000, each incorporated herein by reference in its entirety.

TECHNICAL FIELD

The present invention relates to a chromatography column and, more in particular, a chromatography-column assembly of the direct-heating type.

BACKGROUND ART

A number of technical solutions are already known in which the capillary column is subjected to direct heating by means of an electrically conductive element which is set in contact with the capillary column and electrically powered in a controlled way.

Such an approach makes it possible to obtain various advantages, among which the considerable reduction in the electrical energy required for heating the capillary column and the rapid response of the system to the temperature programs that are set in the course of the analysis.

A number of the various possibilities of obtaining direct heating of the column are, for example, illustrated in U.S. Pat. No. 5,808,178 and in the corresponding international patent application No. WO 97/14957 in the name of Thermedics. Among the various solutions proposed, an assembly is illustrated comprising a column made of fused silica inserted in a tube made of steel, the latter having an internal diameter greater than the external diameter of the column for enabling insertion of the column itself. The steel tube is in turn coated with an insulating sheath made of woven glass fibres.

Another example is described in the U.S. Pat. No. 5,611,846 by Overton et al. For heating the column, this document suggests inserting the column into a sheath together with a conductive filament, or else inserting the column directly into a tube made of conductive material. In a publication by the same authors ("Novel Column Heater for Fast Capillary Gas Chromatography"; Overton et al.—Journal of Chromatographic Science—Vol. 34—December, 1996) it is emphasised that the proposed solution of inserting a capillary column directly into a tube made of conductive material is theoretically preferable for obtaining optimal heating of the column itself, but it is also noted that this solution has proven impracticable due to breakages that occur in the proximity of the sealed ends of the column assembly. This is mainly due to the different thermal coefficients of expansion of the materials.

Other examples of column assemblies of a direct-heating type may be found in the U.S. Pat. No. 5,114,439 by Yost et al., as well as in the U.S. Pat. No. 5,005,399 by Holtzclaw et al.. The columns illustrated in these documents are made of silica and coated with a layer of conductive material, in particular aluminium.

However, on account of the different coefficients of thermal expansion of the materials, there occur frequent breakages of the capillary column or of the conductive coating deposited thereon.

Another example of a direct-heating column for chromatography is illustrated in the U.S. Pat. No. 4,484,061 by Zelinka and Sims. Wound in a spiral on the column is at least one thin film of conductive material enclosed between two electrically insulating films. Fixing to the column during fabrication is ensured by an adhesive, and the assembly is then further coated with a spiral sheath. A construction of this kind, in addition to being particularly complicated and laborious, may prove far from suitable for withstanding high temperatures on account of the use of adhesives. In addition, in the absence of direct contact between the conductive heating material and the column, it is difficult to guarantee uniform heating of the column itself.

Given the above, the object of the present invention is to provide a chromatography-column assembly that enables perfectly uniform direct heating of the column throughout its length.

Another object of the present invention is to provide a chromatography-column assembly capable of withstanding of direct heating of the capillary column at high temperatures.

A further object of the present invention is to provide a particularly simple and economical method for making a direct-heating column assembly of the type referred to above.

DISCLOSURE OF INVENTION

These objects are achieved by the present invention, which relates to a direct-heating column assembly for chromatography, of the type comprising at least one capillary column and at least one element made of electrically conductive material in contact with the capillary column, characterised in that the element made of conductive material comprises a plurality of filaments woven together to form a tubular mesh that envelops the capillary column. There is thus obtained a geometrical symmetry that is particularly effective for guaranteeing a uniform transmission of heat to the column and an optimal distribution of temperature over the entire surface thereof.

According to a peculiar aspect of the present invention, the inner surface of the tubular mesh made of electrically conductive material is set in close contact with the outer surface of the capillary column. The heating element made in the form of a tubular mesh, unlike the known solutions, enables a more intimate contact between the column and the heating element also during sudden changes in temperature.

In addition, in the case where the mesh made of electrically conductive material is used not only as heating means but also as sensor means for detecting the temperature of the column, it is thus possible to obtain also a high precision in the control of the temperature of the column.

The capillary column can be made of an electrically insulating material, such as fused silica, which is widely used for making capillary columns designed for chromatography equipment. As an alternative, the capillary column can be also made of conductive material, in particular metal, and can be coated externally with electrically insulating material to prevent contact between the capillary column and the heating element.

The column assembly according to the invention further comprises a tubular coating sheath that envelops the tubular mesh made of electrically conductive material.

According to a possible embodiment, the tubular coating sheath, consisting of electrically and thermally insulating material, is made up of a plurality of woven filaments. This enables the coating sheaths to be made with materials particularly resistant to heat, for example filaments made of ceramic fibre, glass fibre or other insulating material, thus affording the possibility of using the column also at relatively high temperatures.

The mesh structure of the heating element and of the coating sheath gives on the column assembly a high flexibility and enables compensation of the different thermal expansion of the materials without altering the performance of the column itself.

According to a possible embodiment, the insulating sheath can be set in close contact with the outer surface of the tubular mesh made of electrically conductive material.

Alternatively, the tubular sheath made of insulating material can have a section of a diameter greater than the tubular mesh set on the column, in such a way as to enable the possible circulation of a heat-exchange fluid for obtaining rapid cooling of the column, or else a more homogeneous distribution of heat throughout the column.

The invention further relates to a method for making a chromatography-column assembly of a direct-heating type, characterised by providing the weaving of a plurality of filaments made of electrically conductive material to form a tubular mesh around a capillary column.

It is therefore possible to produce the column assembly according to the invention by weaving the tubular mesh made of electrically conductive material directly on a capillary column made of fused silica or on a column made of metal coated externally with insulating material.

Also the formation of the tubular sheath of insulating coating on the tubular mesh made of electrically conductive material can be produced equally simply in the same way.

The simplicity of construction of the column assembly according to the invention may thus be appreciated, as well as the possibility of obtaining the production of such a column assembly at limited costs.

BRIEF DESCRIPTION OF DRAWINGS

Further characteristics and advantages of the present invention will appear more clearly from the following description, provided purely by way of non-limiting illustrative example with reference to the attached drawings, in which.

MODES FOR CARRYING OUT THE INVENTION

Figure 1:
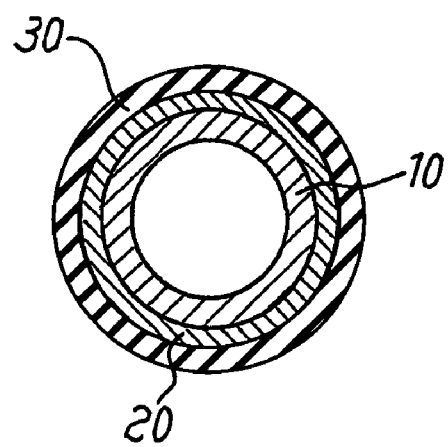
FIG. 1 is a cross-sectional view of a column assembly according to a possible embodiment of the invention.
Figure 2:
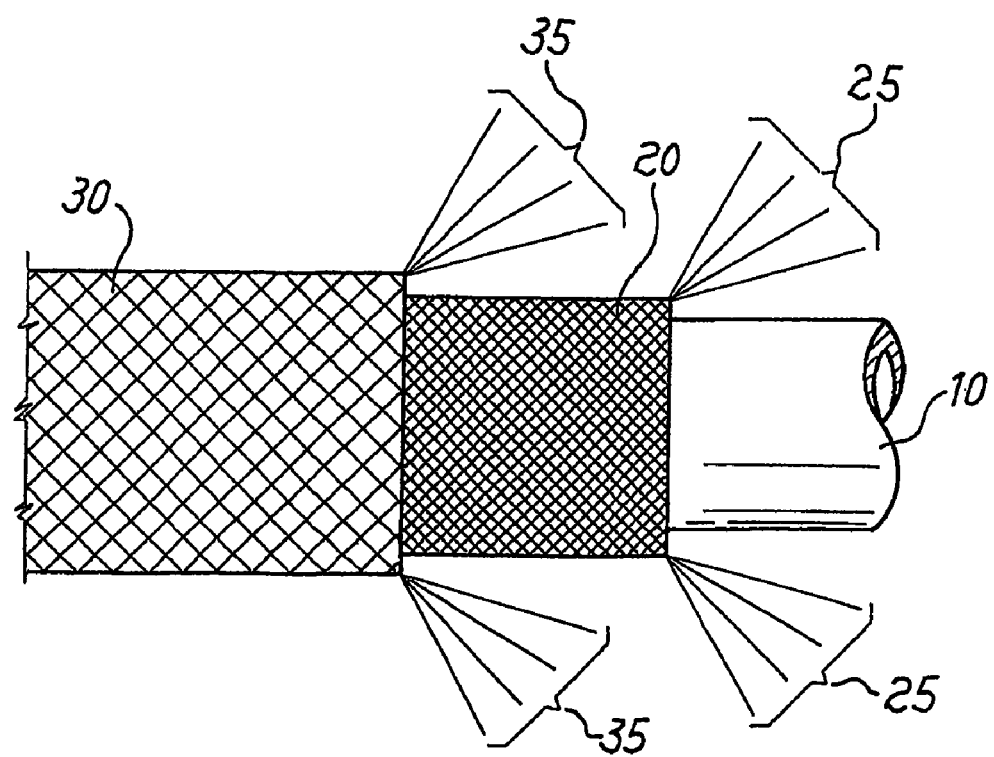
FIG. 2 illustrates the composition of a portion of the column assembly of FIG. 1.

With reference firstly to FIGS. 1 and 2, a column assembly according to the present invention comprises a capillary column 10, made, for example, of fused silica, enveloped in a tubular mesh 20 made of electrically conductive material. The tubular mesh 20 is in turn surrounded by a tubular sheath 30 made of insulating material.

As an alternative to the embodiment here illustrated purely by way of example, the capillary column 10 can also be made of metal, for instance steel or other suitable conductive metals; and be coated externally with insulating material, consisting, for example, of a polyamide sheath, to prevent contact between the metal capillary column and the tubular mesh 20.

The tubular mesh 20 is formed by weaving together a plurality of thin filaments 25 made of an electrically conductive material, such as nickel, or anyway any material, whether metallic or non-metallic, having suitable characteristics of electrical conductivity.

As compared to the known solutions, which provide a single conductive wire set alongside the column or a conductive tube that houses the column inside it, the conductive element with tubular mesh offers a greater reproducibility of the electrical characteristics in that the variability of the parameters of these known conductive elements (section, length, contact, expansion, etc.) is greater than the summation of the individual filaments that form the mesh.

Also to be considered is the advantageous possibility of making a heating element in form of tubular-mesh using woven filaments made of conductive materials having electrical and thermal characteristics different from one another. This enables production of a conductive element having a "new electrical or thermal characteristic" that can be exploited in particular applications, for example a desired variation in overall resistivity of the heating element according to the temperature.

The conductive element made in the form of a mesh 20 is woven preferably in close contact with the column, without, however, being integral with it. The mesh can thus "be deformed" with respect to the column, following upon the difference of expansion of the individual conductive filaments with respect to the column, but the mesh structure is intrinsically capable of absorbing such "deformations" without any breaks occurring at the ends of the assembly, as instead occurs in some solutions proposed in the known art for direct heating of the column, such as, for example, a tube made of electrically conductive material.

The greater flexibility of the assembly enables, in addition, other advantages, such as that of reducing the radius of curvature of the column assembly, as well as that of enabling the use of capillary columns having a relatively large internal diameter.

By supplying electrical energy to the ends of the tubular mesh 20 made of electrically conductive material, it is thus possible to obtain direct heating of the column 10 with perfectly homogeneous transmission of heat, thanks to the geometrical symmetry of the section. The tubular mesh 20 can also be used as sensor means for determining the temperature of the capillary column with high precision. For controlling the heating of the column it is advantageously possible to utilise a system such as the one described in the prior Italian patent application No. Ml99A-002708 in the name of the same Applicant.

Wrapped around the tubular mesh 20 is a tubular coating sheath 30 formed by weaving a plurality of filaments 35 made of electrically insulating material, or more preferably a material simultaneously having electrical and thermal insulating characteristics. The filaments 35 can be made, for example, of ceramic fiber or glass fiber, which are materials having the required insulating characteristics, in addition to having the capacity of withstanding high temperatures. For example, ceramic fibers can withstand temperatures higher than 500° C., in particular even up to a 1000° C. These temperatures are far higher than the maximum limit of the temperature range (from approximately −100° C. to approximately +450° C.) to which a chromatography column of a known type is subjected during use.

Other materials having suitable insulating characteristics and characteristics of resistance to high temperatures may, however, be used.

In the embodiment illustrated in FIGS. 1 and 2, the tubular mesh 20 made of electrically conductive material is set in contact with the capillary column 10, and the tubular sheath 30 made of insulating material envelops the tubular mesh 20 that is in contact with it.

It should be emphasised that, in a column assembly thus made, the heating element and the insulating sheath are not integral with one another even though they are set substantially in close mutual contact. This structure thus enables compensation of the inevitable differences in thermal expansion of the materials used, hence without any problems of breaking of the column assembly thus arising.

Figure 3:
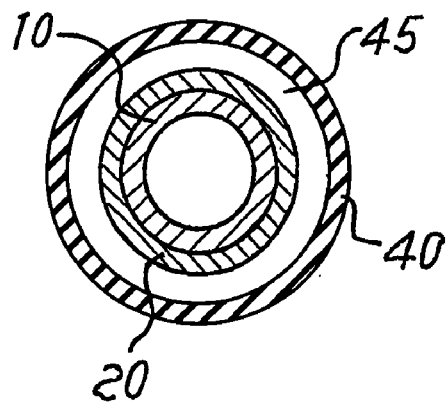
FIG. 3 is a cross-sectional view of a column assembly according to an alternative embodiment of the invention.
Figure 4:
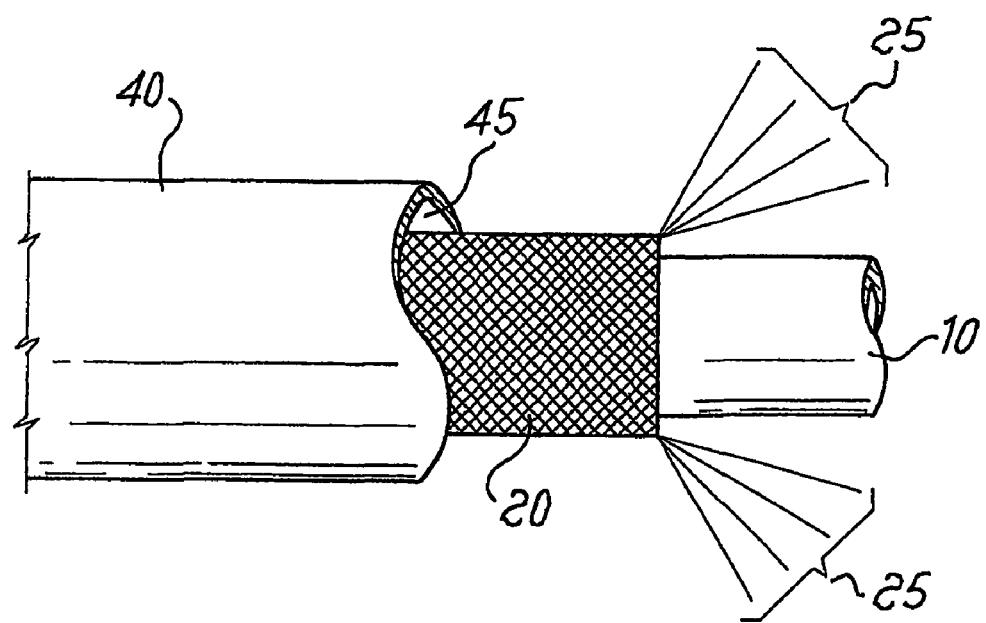
FIG. 4 illustrates the composition of a portion of the column assembly of FIG. 3.

FIGS. 3 and 4 illustrate an alternative embodiment of the invention, for which the same reference numbers have been preserved for identifying parts in common with the previously illustrated embodiment.

As in the case of the previous embodiment, the column assembly of FIGS. 3 and 4 comprises a capillary column 10 made of fused silica on which there is wound in close contact a tubular mesh 20 formed by filaments 25 made of conductive material. Also in this case, the capillary column 10 may, however, be made of metal and be appropriately coated externally with electrically insulating material to prevent contact between the column 10 and the conductive element 20.

The assembly thus formed is housed inside of a tubular sheath 40 made of insulating material having an internal diameter greater than the external diameter of the tubular mesh 20. This enables formation of a gap 45, in which a heat-exchange fluid can be made to circulate to speed up cooling of the column or to render distribution of the heat in the column assembly thus made more uniform.

The tubular insulating sheath 40 can, for instance, be made with a film of plastic material, for example polyamide or other suitable plastic materials. Alternatively, the tubular sheath can be made in the form of a tube of plastic material, or else metallic material, with an internal coating made of plastic or, in any case, an electrically insulating material.

To make a column assembly according to the present invention it is possible to use machines of a known type that produce tubular meshes wound on supports of circular section, for instance the same machines used in the production of shielded electrical cables or the like, possibly modified to be suitable to treat the materials that constitute the column assembly according to the invention.

The method of production of the column assembly according to the invention is particularly simple to put in practice. On the capillary column 10 there is first "woven", in close contact with the column, a tubular mesh 20 formed by a plurality of filaments 25 made of conductive material.

On top of the tubular mesh 20, there can then be woven the tubular sheath 30, in close contact with the underlying mesh 20, by weaving together a plurality of filaments 35 made of insulating material to obtain a column assembly as illustrated in FIGS. 1 and 2.

Alternatively, the column assembly represented in FIGS. 3 and 4 can be obtained simply by sliding the column 10 with the respective tubular mesh 20 into the tubular insulating sheath 40.

There are thus produced, in a continuous way and at limited costs, column assemblies that can then be cut to obtain direct-heating columns for chromatographic equipment having any desired length.

Various modifications, above all as regards the materials, can be made with respect to the embodiments illustrated purely by way of example, without departing from the scope of the present invention.

For instance, filaments made of different insulating materials can be woven together to form the tubular coating sheath if it is desired to give particular properties on the coating itself. The tubular sheath 30 itself produced with the filaments 35 made of insulating material can possibly be formed with a diameter greater than that of the tubular mesh 20 and of the column 10 if it is desired to keep the insulating sheath 30 at a distance from the rest of the assembly, irrespective of whether there is provided the circulation of a heat-exchange fluid in the gap which is thus formed. If, however, the circulation of a fluid is provided in the gap, the seal of the "enlarged" sheath 30 may, for instance, be made with possible films of coating inside and/or outside the sheath 30.

The embodiment of the column assembly according to the invention may be conveniently adapted to the configuration that a column has when it is installed in equipment for chromatography, i.e., the configuration of a winding with a number of turns.

The invention claimed is:

1. A direct-heating column assembly for chromatography, comprising at least one capillary column and at least one element made of electrically conductive, radially deformable material in direct contact with said capillary column, wherein said element made of conductive material is formed exclusively by a plurality of conductive filaments woven together to form a tubular mesh having an inner surface that uniformly heats said capillary column both in radial and longitudinal directions.

2. A chromatography-column assembly according to claim 1, wherein electric power is supplied at opposed ends of said tubular mesh.

3. A chromatography-column assembly according to claim 1, wherein the inner surface of said tubular mesh made of electrically conductive material is set in close contact with the outer surface of said capillary column.

4. A chromatography-column assembly according to claim 1, further comprising a tubular coating sheath that envelops said tubular mesh made of electrically conductive material.

5. A chromatography-column assembly according to claim 4, wherein said tubular coating sheath is made of electrically insulating material.

6. A chromatography-column assembly according to claim 4, wherein said tubular coating sheath is made of thermally insulating material.

7. A chromatography-column assembly according to claim 4, wherein said tubular coating sheath is made with a material capable of withstanding temperatures higher than 400° C.

8. A chromatography-column assembly according to claim 4, wherein said tubular coating sheath made of insulating material is formed by a plurality of woven filaments.

9. A chromatography-column assembly according to claim 4, wherein said tubular coating sheath made of insulating material is formed by a film.

10. A chromatography-column assembly according to claim 4, wherein the inner surface of said tubular coating sheath made of insulating material is set in close contact with the outer surface of said tubular mesh made of electrically conductive material.

11. A chromatography-column assembly according to claim 4, wherein said tubular coating sheath made of insulating material has a diameter greater than said tubular mesh made of electrically conductive material.

12. A chromatography-column assembly according to claim 1, wherein said tubular mesh made of electrically conductive material constitutes a heater for said capillary column.

13. A chromatography-column assembly according to claim 12, wherein said tubular mesh made of electrically conductive material constitutes a sensor to determine the temperature of said capillary column.

14. A chromatography-column assembly according to claim 1, wherein said capillary column is made of fused silica or another suitable electrically insulating material.

15. A chromatography-column assembly according to claim 1, wherein said capillary column is made of electrically conductive material, and is coated externally with electrically insulating material in order to electrically insulate said column with respect to said tubular mesh made of electrically conductive material.

16. A chromatography-column assembly according to claim 15, wherein the electrically conductive material of the capillary column comprises metal.

17. A method for making a direct-heating column assembly for chromatography, comprising:
providing a capillary column;
weaving a plurality of filaments made of electrically conductive material around and in direct contact with the capillary column to form a radially deformable tubular mesh; and
uniformly heating said capillary column both in radial and longitudinal directions with the tubular mesh.

18. A method according to claim 17, wherein the weaving of a plurality of filaments made of electrically insulating material is further provided to form a tubular sheath around said tubular mesh made of electrically conductive material.

19. A method according to claim 17, wherein the weaving of a plurality of filaments made of thermally insulating material is further provided to form a tubular sheath around said tubular mesh made of electrically conductive material.

20. A method according to claim 17, further comprising inserting said capillary column and said mesh made of electrically conductive material woven on said column into a tubular coating sheath having a diameter greater than that of said column and of said tubular mesh.

21. A chromatography-column assembly according to claim 1, wherein said element is flexible.

22. A chromatography-column assembly according to claim 1, wherein said element is thermally stress-resistant.

23. A direct-heating column assembly for chromatography comprising at least one capillary column and at least one element made of electrically conductive, radially deformable material in direct contact with said capillary column, wherein said element made of conductive material is formed only by a plurality of conductive filaments woven together to form a tubular mesh having an inner surface that uniformly envelops and heats said capillary column both in radial and longitudinal directions, said tubular mesh also constituting a sensor to determine a temperature of said capillary column.

24. A chromatography-column assembly according to claim 4, further comprising a gap spacing an inner surface of the tubular coating sheath and an outer surface of said tubular mesh.

25. A method according to claim 17, further comprising forming said tubular mesh exclusively from said plurality of electrically conductive filaments.

* * * * *